(12) United States Patent
Van Saarloos et al.

(10) Patent No.: US 6,575,963 B1
(45) Date of Patent: Jun. 10, 2003

(54) LASER SCANNING APPARATUS AND METHOD

(75) Inventors: Paul Phillip Van Saarloos, Karrinyup (AU); Philip George Reid, Wanneroo (AU)

(73) Assignee: The Lion Eye Institute of Western Australia Incorporated (AU)

( * ) Notice: Subject to any disclaimer, the term of this patent is extended or adjusted under 35 U.S.C. 154(b) by 0 days.

(21) Appl. No.: 09/484,774

(22) Filed: Jan. 18, 2000

Related U.S. Application Data

(63) Continuation of application No. PCT/AU98/00555, filed on Jul. 16, 1998.

(30) Foreign Application Priority Data

Jul. 16, 1997 (AU) .............................................. PO7903

(51) Int. Cl.[7] .............................................. A61B 18/18
(52) U.S. Cl. ................................ 606/10; 606/4; 606/5; 606/17; 359/209
(58) Field of Search ................................ 606/2, 4, 5, 6, 606/9, 10, 11, 12, 13, 14, 17; 359/196–210

(56) References Cited

U.S. PATENT DOCUMENTS

| | | |
|---|---|---|
| 4,712,887 A | 12/1987 | Baer |
| 4,718,418 A | 1/1988 | L'Esperance, Jr. |
| 4,973,848 A | 11/1990 | Kolobanov et al. |
| 5,474,549 A | 12/1995 | Ortiz et al. |
| 5,490,849 A * | 2/1996 | Smith .............................. 606/5 |
| 5,520,679 A | 5/1996 | Lin |
| 5,558,666 A * | 9/1996 | Dewey et al. .................. 606/9 |
| 5,957,915 A * | 9/1999 | Trost ............................. 606/13 |

FOREIGN PATENT DOCUMENTS

| | | |
|---|---|---|
| EP | 0534222 | 3/1993 |
| GB | 1513249 | 6/1978 |
| GB | 2220501 | 1/1990 |

OTHER PUBLICATIONS

D.P. Rowe et al., "Laser Beam Scanning", Proceedings of the Spie., vol. 2088, Oct. 5, 1993, pp. 18–26, XP000614108,* p. 22, line 26–line 30*.

E. A. Watson, "Analysis of Beam Steering With Decentered Microlens Arrays", Optical Engineering, U.S. Soc. of Photo–Optical Instrumentation Engineers, Bellingham, vol. 32, No. 11, Nov. 1, 1993, pp. 2665–2670, XP000413673, ISSN: 0091–3286.

M. E. Motamedi et al., "Microoptic Laser Beam Scanner", Proceedings of the Spie, vol. 1992, Jul. 14, 1993, pp. 2–13, XP000614022, *p. 1, line 33–line 39*.

* cited by examiner

*Primary Examiner*—Roy D. Gibson
(74) *Attorney, Agent, or Firm*—Baker Botts LLP

(57) ABSTRACT

The present invention provides a method for scanning material with a laser beam including directing a laser beam (20) through a scanning means, wherein said scanning means includes a first lens (11) and a second lens (12) separated by a distance (16) approximately equal to the focal length of the lenses. The method includes controlling the beam (20) by moving at least one of the lenses in a plane perpendicular to the beam to scan the material. The invention also provides a scanning apparatus for scanning material with a laser beam including laser means for producing a beam of ultraviolet or infra-red light, scanning means for scanning the laser source in a predetermined pattern onto an area of the material, and controlling means for controlling the scanning means, wherein the scanning means includes two lenses, separated by approximately the focal length of one of the lenses, with at least one of the lenses movable perpendicular to the beam to scan the beam.

29 Claims, 3 Drawing Sheets

LASER SCANNING APPARATUS AND METHOD

This is a continuation of copending International application No. PCT/AU98/00555 filed Jul. 16, 1998.

The present invention relates to the field of laser processing or ablation of materials, and is of application in, for example, the field of laser procedures for the refractive correction of the eye, in operations such as photorefractive keratectomy (PRK) and laser in-situ keratomileusis (LASIK).

Refractive surgery is currently performed with the excimer laser, which operates at a wavelength of 193 nm. A laser delivery system is used in these procedures to control the shape that is etched onto the cornea. The ablated shape can be controlled by a variety of methods, including the use of a large beam, or a scanning beam, combined with masks, templates or diaphragms (see, for example, U.S. Pat. No. 5,474,549). Other systems include apparatus that scan the beam across the area to be ablated in a predetermined pattern.

Large beam control system using masks and diaphragms require large, high energy laser sources, which entail increased running and maintenance costs. These systems are also inflexible and limited in their ability to produce complicated shapes on the material to be ablated. In comparison, scanning methods require smaller, lower energy laser sources, making them more space and cost efficient. It is also easier to control the desired shape of the ablation using a scanning method (Ren, Simon and Parel, 1993).

Different mechanisms for scanning the beam across the surface to be ablated have been suggested in a number of prior art patents. U.S. Pat. No. 4,718,418 teaches the use of a commercially available scanning unit to scan a rounded-square spot of 0.5 mm by 0.5 mm across the surface to be scanned. The inventors suggest that no overlap should occur between individual pulses, with the areas of greater tissue removal, such as the central cornea in a myopic correction, to be scanned with the square dot more often than those areas with less material to be removed.

U.S. Pat. No. 5,520,679 describes a scanning method using a low power, high repetition rate laser. Uniform beam density or a specific spot shape is not required. The galvanometer scanning device is coupled with a computer controller, and synchronized with the laser's repetition rate to move in predetermined patterns. A mathematical model for optimum beam overlap is provided, indicating that ablations should overlap between 50% and 80% to avoid a ridged corneal surface.

As described above, electrical galvanometer scanners have been used as mechanisms for scanning the laser beam in prior art devices. These scanning systems utilise mirrors mounted on galvanometer apparatus, which thereby produce a motion to move the mirrors to scan the beam in a predetermined pattern in X or Y or X-Y directions. However, a number of disadvantages are associated with galvanometer scanning systems. The amount of light reflected by the mirrors in such systems is dependent on the angle of these mirrors. Changing the angle of the galvanometer mounted mirrors may alter the energy of the laser beam delivered to the cornea. The beam path length may also be affected by the galvanometer mirrors. Any change to the path length may subsequently result in a loss of beam focus. If the distance from the scanner to the eye is not well controlled, then the position of the laser as it hits the eye cannot be properly predicted and the resultant surgery will be inaccurate.

It is therefore an object of the present invention to provide an improved scanning laser beam control system that can overcome one or more of the limitations of the prior art scanning systems and more accurately and predictably ablate a desired shape into a material.

It is a further object of the present invention to provide a scanning system that can be more easily fitted to non-scanning laser systems.

Thus, according to the present invention there is provided a laser scanning method for scanning material with a laser beam including directing a laser beam through a scanning means, wherein said scanning means includes a first lens and a second lens, the two lenses separated by a distance approximately equal to the focal length of one of the lenses, and said method includes directing said beam through said lenses in turn to said material, and controlling said beam by moving at least one of said lenses in a plane perpendicular to said beam to scan said material with said beam.

Preferably said method includes passing said beam through said second lens after said first lens, and the two lenses are separated by a distance approximately equal to the focal length of said second lens.

Preferably the method includes providing said laser beam by means of an Argon-Fluoride excimer laser (193 nm) or a solid state UV laser (190–215 nm) such as quintupled Nd:YAG lasers, or infra-red lasers such as Ho:YAG or Er:YAG lasers.

Preferably the method includes controlling the scanning means to scan the laser beam, and more preferably in predetermined patterns.

Preferably the method includes controlling said scanning means by means of computer means.

The first lens may have a focal length substantially longer than the second lens.

The present invention also provides a scanning apparatus for scanning material with a laser beam including laser means for producing a laser beam, scanning means for scanning the laser beam in a predetermined pattern onto the material; and wherein said scanning means includes two lenses, separated by a distance approximately equal to the focal length of one of the lenses, and at least one of said first and second lenses is mounted for movement perpendicular to said beam to scan said beam.

Preferably said first and second lenses are arranged so that said beam passes through said second lens after said first lens, and the two lenses are separated by a distance approximately equal to the focal length of said second lens. The first lens is preferably mounted for movement perpendicular to the laser beam.

Preferably the laser means is an ablation laser, and more preferably the laser means is an UV ablation laser such as an Argon fluoride excimer laser, quintupled Nd:YAG, or a quadrupled Ti:Sapphire laser, or an infra-red ablation laser such as Er:YAG, or an intrastromal ablation laser such as a Ho:YAG, Nd:YAG or Nd:YLF laser. For example, for intrastromal, or lens ablation, the laser means would preferably be a visible or near infra-red laser such as Nd:YAG or Nd:YLF.

Preferably the scanning means is controllable to scan said laser beam, and more preferably to scan said laser beam in predetermined patterns.

Preferably the scanning means is controllable to scan said beam to follow, or compensate for, movements of said material.

Thus, the scanning means can scan the beam to compensate for movement of the material.

Preferably the controlling means includes a microprocessor means or a computer means.

Preferably the apparatus is for scanning a laser across the cornea of an eye in surgical procedures such as PRK, LASIK, intrastromal ablation, or across the lens in a phaco-emulsification procedure.

One of the two lenses may have a focal length substantially longer than the other.

Preferably the apparatus is for scanning skin with any one of various laser beams by directing any one of said laser beams through said scanning means.

The present invention further provides a method for ablating human or animal tissue including directing a laser beam through a scanning means onto an area of said tissue to thereby ablate said tissue, wherein said scanning means includes two lenses, separated by a distance equal to the focal length of one of the lenses, and said method includes controlling said beam by moving at least one of said lenses in a plane perpendicular to said beam to scan said material with said beam.

Preferably said tissue is corneal tissue.

Alternatively said tissue is lens tissue and said method is for breaking up a lens prior to cataract surgery.

Preferably said method is used to correct refractive errors of eyesight, by PRK, LASIK or intrastromal ablation.

Preferably the scanning means is controllable to scan the laser beam.

Preferably the scanning means is controllable to scan the laser beam in predetermined patterns and/or follow movements of said material.

In one preferred embodiment, there is provided a laser scanning method for scanning skin with various laser beams by directing said laser beams through said scanning means.

In another preferred embodiment, there is provided a scanning apparatus for scanning skin with various laser beams by directing said laser beams through said scanning means.

Preferably said laser beams are provided by any laser used for dermatological uses, hair removal or photodynamic therapy.

Preferably the first lens is mounted in a mount and said mount is attached to a static mount by means of two pairs of linear bearings or slides, and wherein said pairs of bearings or slides are either arranged with respect to each other, or attached to each other, at right angles.

Preferred embodiments of the invention will be described by way of example with reference to the accompanying drawing, in which.

Figure 1:
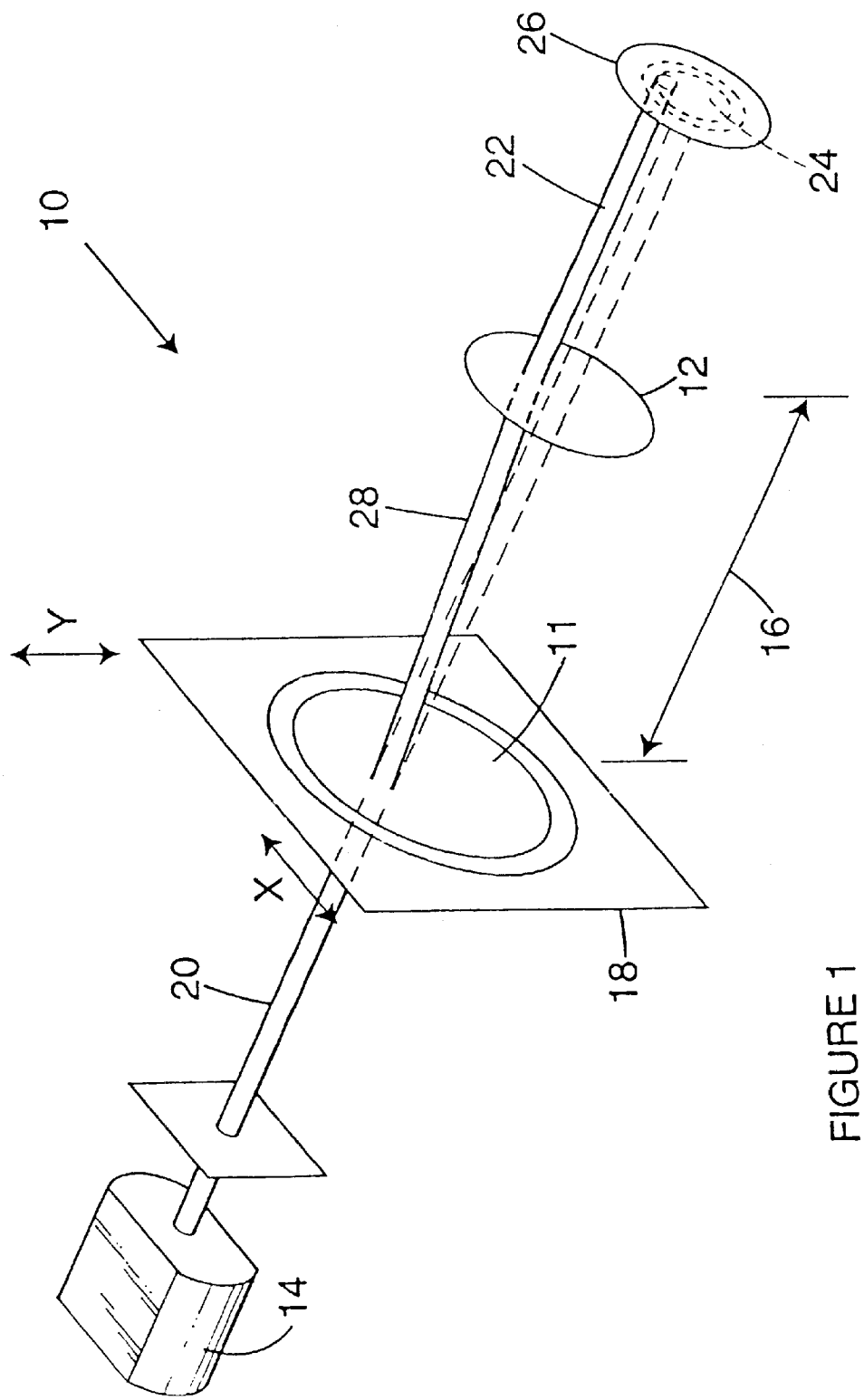
FIG. 1 is a schematic view of an arrangement of a laser scanning apparatus according to the present invention, with an eye under examination.

A laser scanning apparatus for use in laser ablation is shown generally at 10 in FIG. 1. The apparatus 10 includes first and second lenses 11 and 12 and a laser source 14. The distance 16 between the lenses 11 and 12 is approximately equal to the focal length of second lens 12. First or scanning lens 11 is movable in the plane 18 perpendicular to incident laser beam 20, and is manipulated by a computer controlled scan driver. First lens 11 is in the preferred embodiment a low powered, and may be a diverging or a converging lens. By using a focal length for first lens 11 much longer than that of second lens 12, the resolution of controlling the position of the beam on the eye will be much higher than the resolution of controlling the position of first lens 11. Second lens 12 is a converging lens.

In use, the exit beam 22 is scanned over the material being ablated, for example cornea 24 of eye 26, by moving first lens 11 in plane 18 to direct beam 28 through second or focussing lens 12. Exit beam 22 emerges from second lens 12 parallel to original beam 20, but displaced vertically and/or laterally according to the position of first lens 11. Thus, the output of the laser source 14 may be deposited as desired on cornea 24.

Figure 2B:
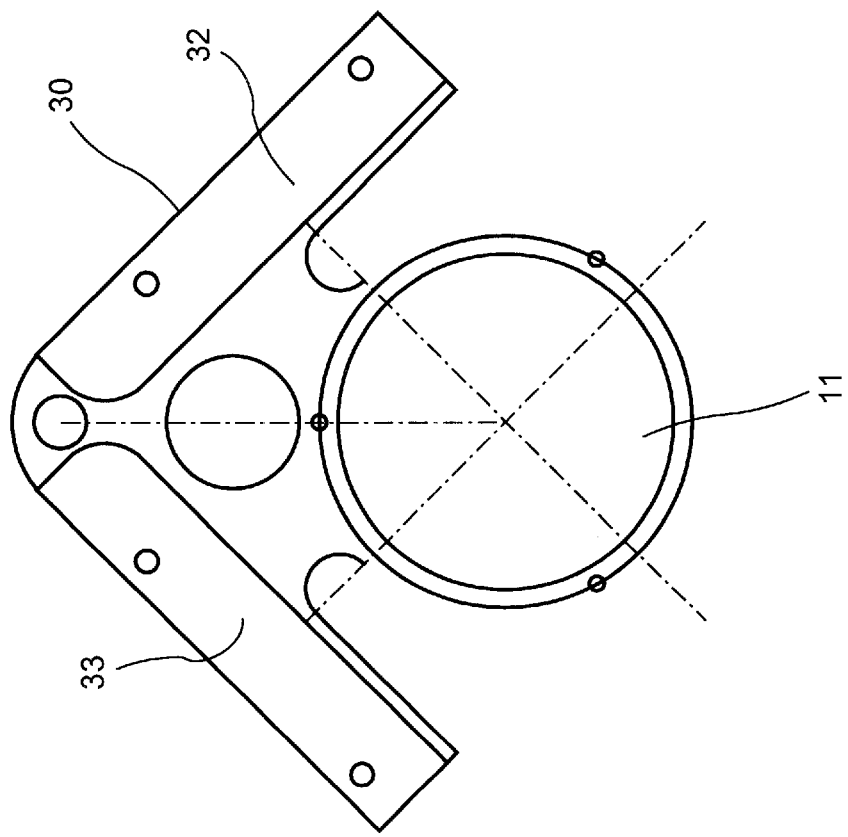
FIG. 2B is a plan view of the lens holder frame of the first lens of the laser scanning apparatus of FIG. 1.
Figure 2A:
FIG. 2A is a side view of the lens holder frame of the first lens of the laser scanning apparatus of FIG. 1.
Figure 3:
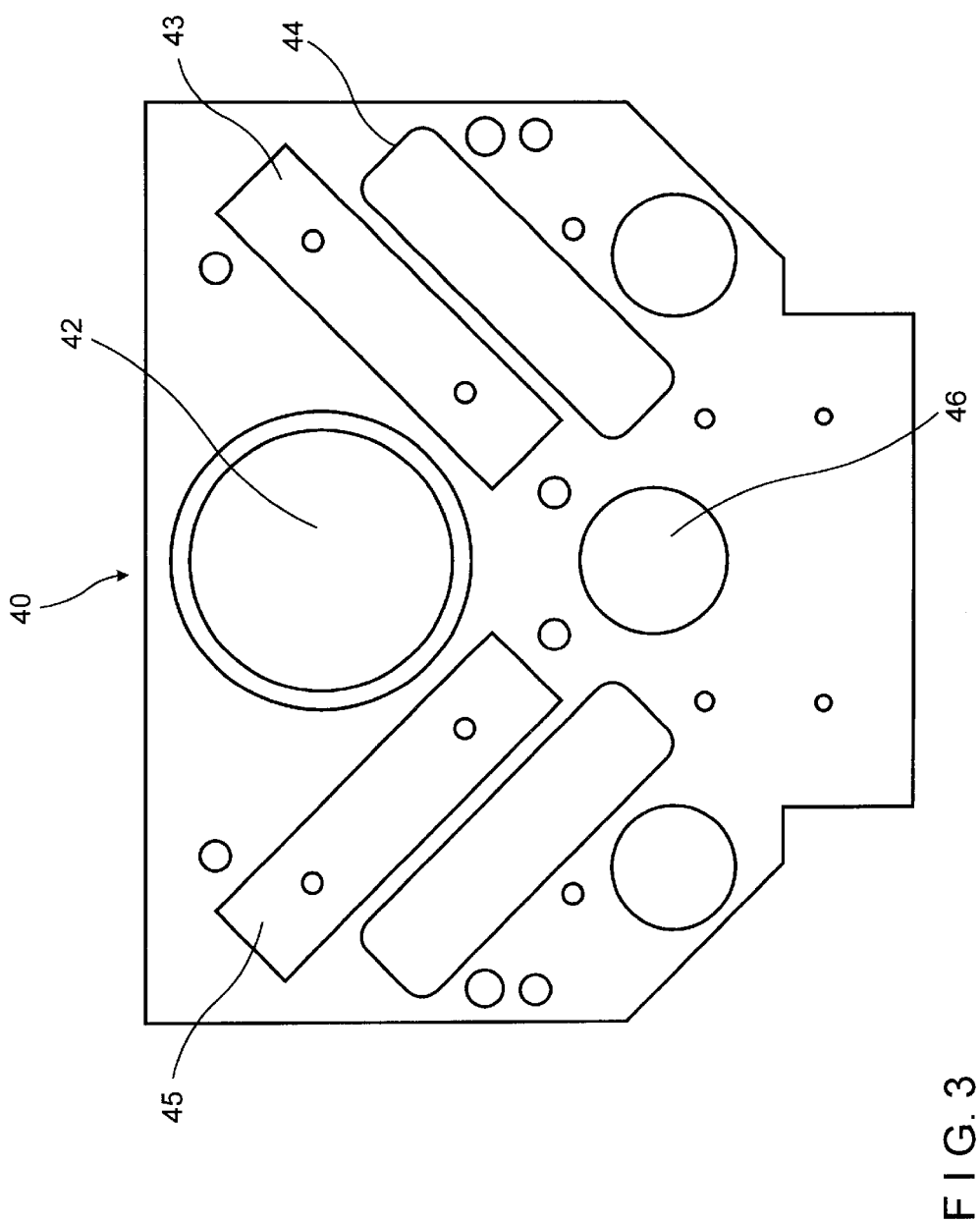
FIG. 3 shows a plan view of the scanner mount of the laser scanning apparatus of FIGS. 2A and 2B.

The first lens 11 is mounted in a frame or holder 30. The holder 30 with first lens 11 is shown in FIGS. 2A and 2B. The holder 30 is preferably made of a material which is light and corrosion-resistant, such as aluminium.

A pair of linear bearings (not shown) are joined together at right angles and mounted between lens holder 30 and static mount 40, attached at points 43 and 32. A second pair of right angle bearings are mounted at points 33 and 45. The lens holder 30 sits in apposition with mount 40, and the motors, bearings and electronics which drive the first lens 11 in the lens holder 30 are connected through it. Mount 40 includes an independent position sensor 42 and drive access aperture 44. The beam 20 passes through aperture 46 (in front of which is located the first lens 11).

The bearings may be linear bearings, or most preferably, high quality linear slides. They are arranged such that the first lens 11 is movable in any direction: it may be moved in the Y direction (up or down), the X direction (left to right) or XY direction (up and right or down and left etc.). The beam 28 can thereby be scanned in a circle or moved to trace any desired pattern.

DC motors with digital encoders are used to drive a linear belt system which in turn, moves the bearings, driving the part where the two 90° bearings are joined. DC motors with −0.013 mm resolution may be used, such that the lens can be moved to any arbitrary place on an approximately 40 mm×40 mm area, which approximates an arbitrary grid of 3000 by 3000 encoder counts. This may correspond to the beam being directed to an approximately 10 mm×10 mm grid on the eye. A digital position controller, such as one based on HP HCTL 1100, is used to produce the signal that drives the motors. A pulsewidth modulator amplifier is used to amplify the signal from the controller and propel the motors. Software is used to determine the direction and speed of the movements.

Any suitable combination of lenses may be used according to the requirements of the laser source. In one arrangement, used with an excimer laser, two plano-convex lenses may be used. The scanning lens 11 has a focal length of around 1.0 meter. The focussing lens 12, also plano-convex, has a focal length of around 280 mm. The second lens 12 is thus placed about 280 mm behind the scanning lens 11. In a second arrangement, the scanning lens 11 is a diverging lens with a focal length of around 2.0 meters, and the focussing lens 12 has a focal length of approximately 1.0 meter.

Other arrangements of lenses may include concave/convex or convex/convex. An additional lens may also be included, before the scanning lens or between the scanning and focussing lens. In this type of arrangement, second lens 12 may be a combination of lenses after the scanning lenses.

Two sensor units are also used in the scanner design. Index sensors are used to determine the centre and end positions of the bearings. A redundant sensor, in the form of a linear photodiode, is used to check that the scanner lens travels to the correct software-directed position.

Modifications within the spirit and scope of the invention may be readily affected by those skilled in the art. It is to be understood therefore that this invention is not limited to the particular embodiment described by way of example hereinabove.

What is claimed is:

1. A method for scanning material with a laser beam including directing a laser beam through a scanning mechanism, wherein said scanning mechanism includes a first lens and a second lens, said first and second lenses separated by a distance approximately equal to the focal length of said second lens, and wherein said method includes directing said beam through said second lens after said first lens 1, and controlling said beam by moving at least said first lens in a plane perpendicular to said beam to scan said material with said laser beam.

2. A method as claimed in claim 1, including providing said laser beam by means of an ablation laser.

3. A method as claimed in claim 1 including providing said laser beam using a laser selected from an UV ablation laser, an infra-red ablation laser and an intrastromal ablation laser.

4. A method as claimed in claim 1 including providing said laser beam using a laser selected from an Argon fluoride excimer laser, a quintupled Nd:YAG UV ablation laser, a quadrupled Ti:Sapphire UV ablation laser, an Er:YAG infra-red ablation laser, a Ho:YAG intrastromal ablation laser, a Nd:YAG intrastromal ablation laser and a Nd:YLF intrastromal ablation laser.

5. A method as claimed in claim 1 wherein said first lens has a focal length substantially longer than said second lens.

6. A method as in claim 1, including controlling said scanning means to scan said laser beam in predetermined patterns.

7. A method as claimed in claim 6, including controlling said scanning means by means of computer means.

8. A method as in claim 1, wherein said method is for ablating human or animal tissue.

9. A method as claimed in claim 8, wherein said tissue is corneal tissue.

10. A method as claimed in claim 9, wherein said method is for correcting refractive errors of eyesight.

11. A method as claimed in claim 10, wherein said method is for use in one of photorefractive keratectomy, laser in-situ keratomileusis and intrastromal ablation.

12. A method as claimed in claim 1, wherein said material is the lens of the eye, the laser beam is provided by one of a pulsed visible laser and a pulsed near infra-red laser and the method is for breaking up the lens prior to cataract surgery.

13. A method as in claim 1, wherein said method is for scanning skin with various laser beams.

14. A method as in claim 1, including controlling said scanning to follow, or compensate for, movements of said material.

15. A scanning apparatus for scanning material with a laser beam including a laser for producing a laser beam; and
a scanning mechanism for scanning the laser beam in a predetermined pattern onto the material;
wherein said scanning mechanism includes two lenses arranged so that said beam passes through a second lens after a first lens, and said lenses separated by a distance approximately equal to the focal length of said second lens, and wherein at least said first lens is mounted for movement perpendicular to said beam to scan said beam.

16. A scanning apparatus as claimed in claim 15, wherein said laser is an ablation laser.

17. A scanning apparatus as claimed in claim 15, wherein said laser is one of an UV ablation laser, an infra-red ablation laser and an intrasomal ablation laser.

18. A scanning apparatus as claimed in claim 15, wherein said laser is one of an Argon fluoride excimer laser, a quintupled Nd:YAG UV ablation laser, a quadrupled Ti:Sapphire UV ablation laser, an Er:YAG infra-red ablation laser, a Ho:YAG intrastromal ablation laser, a Nd:YAG intrastromal ablation laser and a Nd:YLF intrastromal ablation laser.

19. A scanning apparatus as claimed in claim 15, further including a controller to control said scanning mechanism to scan said laser beam in predetermined patterns.

20. A scanning apparatus as claimed in claim 19, wherein said controller includes one of a microprocessor and a computer.

21. A scanning apparatus as claimed in claim 19, wherein said material is one of human tissue and animal tissue.

22. A scanning apparatus as claimed in claim 21 wherein said apparatus is for performing refractive corrections of the eye by one of photorefractive keratectomy, laser in-situ keratomileusis and intrastromal ablation.

23. A scanning apparatus as claimed in claim 15 wherein said laser is one of a pulsed visible laser and a pulsed near infra-red laser, and wherein said material is lens tissue of the eye and the apparatus is for breaking up the lens tissue by photodisruption prior to cataract surgery.

24. A scanning apparatus as claimed in claim 15, wherein said apparatus is for scanning skin with any one of various laser beams by directing any one of said laser beams through said scanning mechanism.

25. A scanning apparatus as claimed in claim 24, wherein said laser is any laser source used for one of dermatological uses, hair removal and photodynamic therapy.

26. An apparatus as claimed in claim 15, wherein said scanning mechanism is controllable to scan said beam to follow movements of said material.

27. An apparatus as claimed in claim 15, wherein said first lens is mounted in a mount and said mount is attached to a static mount by means of two pairs of linear bearings or slides, and wherein said pairs of bearings or slides are either arranged with respect to each other, or attached to each other, at right angles.

28. A scanning apparatus as claimed in claim 15 wherein said first lens has a focal length substantially longer than said second lens.

29. An apparatus as claimed in claim 15, wherein said scanning mechanism is controllable to scan said beam to compensate for movements of said material.

* * * * *